NEBULIZER
Original Filed Nov. 2, 1964 2 Sheets-Sheet 1
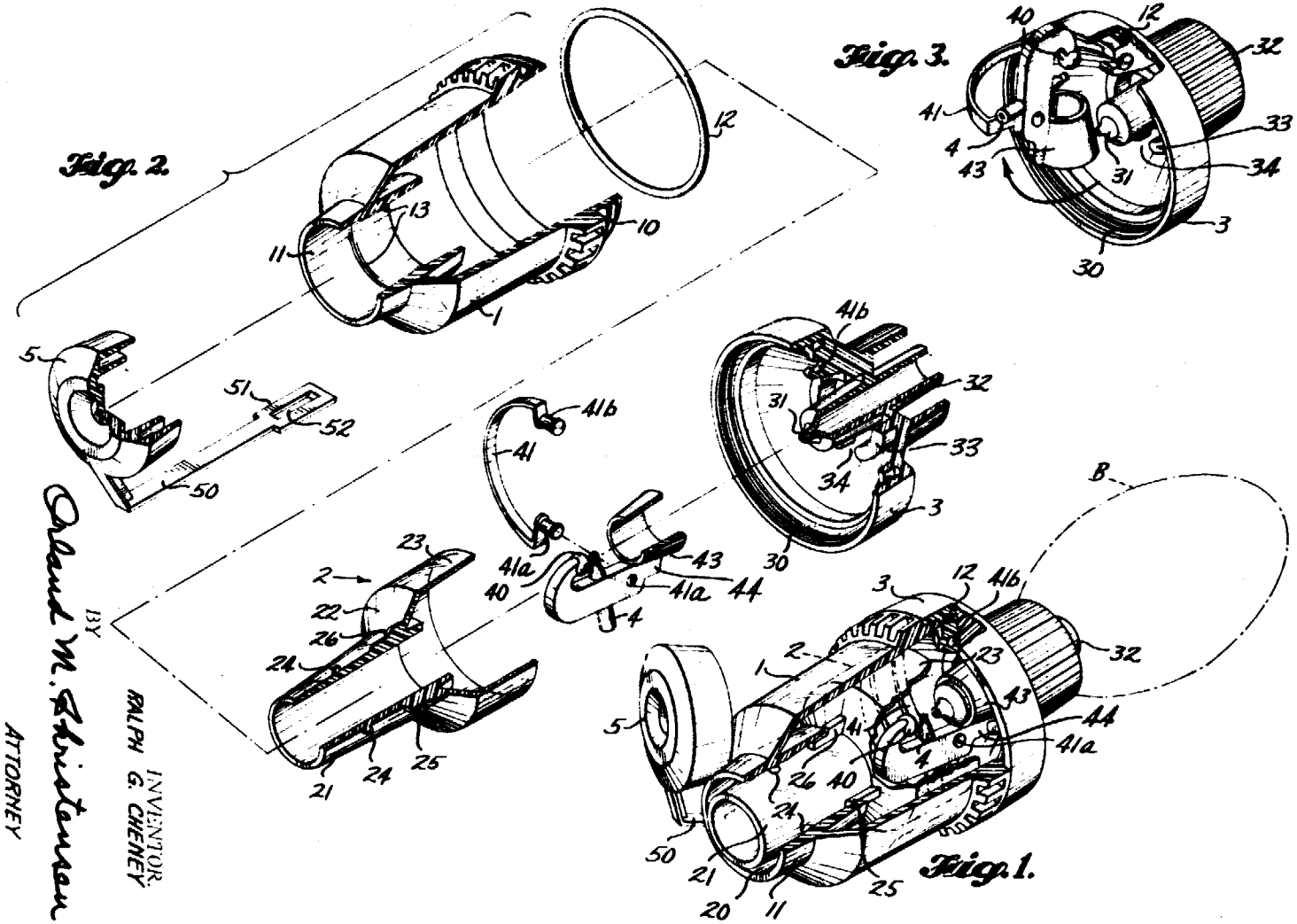
INVENTOR.
RALPH G. CHENEY
BY
Orland M. Christensen
ATTORNEY

NEBULIZER

Original Filed Nov. 2, 1964 2 Sheets-Sheet 2

INVENTOR.
RALPH G. CHENEY

BY

Orland M. Christensen

ATTORNEY

United States Patent Office

Re. 26,626
Reissued July 15, 1969

26,626
NEBULIZER

Ralph G. Cheney, Seattle, Wash., assignor to Air Reduction Company, Incorporated, New York, N.Y., a corporation of New York Original No. 3,269,665, dated Aug. 30, 1966, Ser. No. 408,284, Nov. 2, 1964. Application for reissue Aug. 14, 1968, Ser. No. 758,637
Int. Cl. A61m *11/00*
U.S. Cl. 239—338 12 Claims

Matter enclosed in heavy brackets [ ] appears in the original patent but forms no part of this reissue specification; matter printed in italics indicates the additions made by reissue.

*ABSTRACT OF THE DISCLOSURE*

*A nebulizer with increased air flow and high efficiency is disclosed wherein liquid medicament fog is dispensed by the combined action of primary and secondary air flow through an inner tubular shell fitted within a sleeve coaxially positioned within an outer shell. Primary air directed into the inner end of the inner shell operates an ejector adjacent the nebulizer base. Secondary air is drawn through a longitudinal flow space of substantially annular form between the inner shell and a surrounding outer shell and thereupon flows radially inward through a gap formed between the outer shell and the base of the inner shell so as to mix with the primary air in the vicinity of the ejector. Preferably the inner shell flairs in diameter toward the base over a portion of its longitudinal extent.*

This invention relates to an atomizer or nebulizer of the general character disclosed in my Patent No. 3,069,-097, issued December 18, 1962. Such nebulizers are used to supply a liquid medicament in the form of a fog or mist of minute droplets for the relief of bronchial congestion, asthma, and the like, and sometimes are used in hospitals or clinics for administration of antibiotics or other medicaments.

Such nebulizers function by reason of discharge of primary air (as hereinafter defined) from an inner nozzle within a shell, past the delivery end of a capillary space or tube, the pick-up end whereof communicates with a liquid supply space within the shell, the discharge from the capillary tube impinging a baffle, such as a ball, that breaks it up into fine droplets, and the primary air directs these droplets out through an outer nozzle that projects from the shell, towards which the discharge is directed, and so into the mouth or nasal passages of the user. Normally secondary air enters around the outer nozzle, and exits therefrom with the mist. A closure cap seals the outer end of the outer nozzle to prevent spilling when the nebulizer is not in use, but can be removed and moved aside to permit discharge.

Nebulizers of this general type are commonly molded of plastic. They must be cleaned, internally as well as externally, from time to time, hence the several component parts must be readily separable, yet they must be so formed that when reassembled they will fit accurately, as intended. Some of these component parts are quite small, and when separated or while they are being sterilized they can be easily lost, yet by the present inventon such parts are anchored or joined to principal parts by semipermanent connecting means, such as somewhat flexible ribbons of plastic material, whereby the parts can be separated sufficiently for cleaning, but not ordinarily can they be wholly detached—although complete detachment can be effected by proper manipulation if required.

As part of the structure permitting disassembly and reassembly, yet insuring accurate relative positioning of parts when assembled, the outer nozzle is formed as a tube that is part of an inner shell and projects through and in spaced relation to a sleeve of an outer shell, so as to define a secondary air inlet, the tube and sleeve being so formed and interengageable that they are secure against accidental disengagement, and will snap into correct assembled relationship, and so remain during use.

The function of the secondary air is to augment the primary gaseous vehicle for the mist droplets, and to direct them through the outer nozzle, hence the inner shell is so formed that it will at least divert radially and evenly outwardly inflowing secondary air, and avoid conflict thereof with the counterflowing primary air, and preferably that it will lead the secondary air to a location adjacent or behind the primary air discharge and the droplets picked up thereby, before permitting the secondary air to mingle with the primary air and to flow in the direction of discharge through the outer nozzle.

These objects, and others that will become apparent hereinafter, are achieved according to the present invention by a structure that is simple and inexpensive.

The nebulizer is shown and described herein in preferred and representative forms, and the novel features and combinations incorporated therein will be set forth in the claims.

FIGURE 1 is an isometric view, partly broken away, showing the nebulizer assembled and ready for use.

FIGURE 2 is an exploded isometric view of the parts that are shown assembled in FIGURE 1.

FIGURE 3 is an isometric view of the base and associated separate body, disassembled as for cleaning, but still held one to the other.

Figure 5:
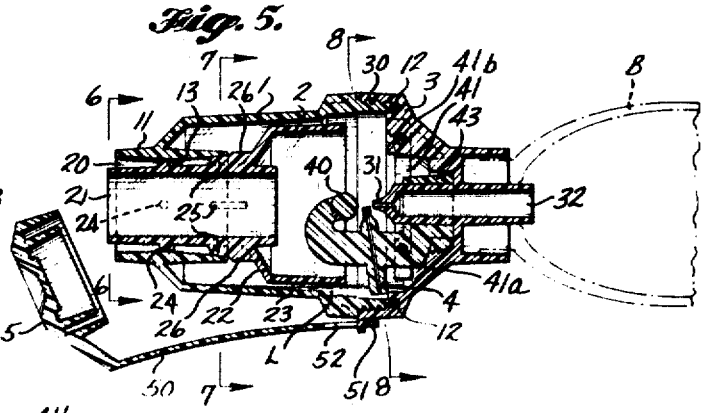
FIGURE 5 is an axial elevation through the nebulizer, with the closure cap removed but not separated from the shell.
Figure 6:
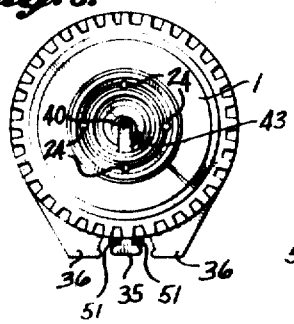
FIGURE 6 is an end elevation of the nebulizer, as seen at the line 6—6 of FIGURE 5.
Figure 8:
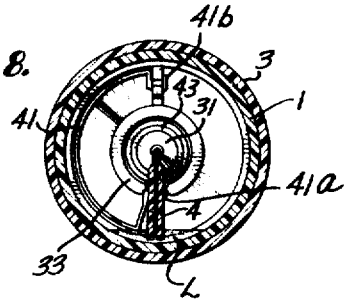
Figure 7:
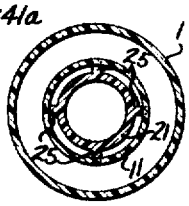

FIGURES 7 and 8 are cross sectional views at the respective lines 7—7 and 8—8 of FIGURE 5.

Figure 4:
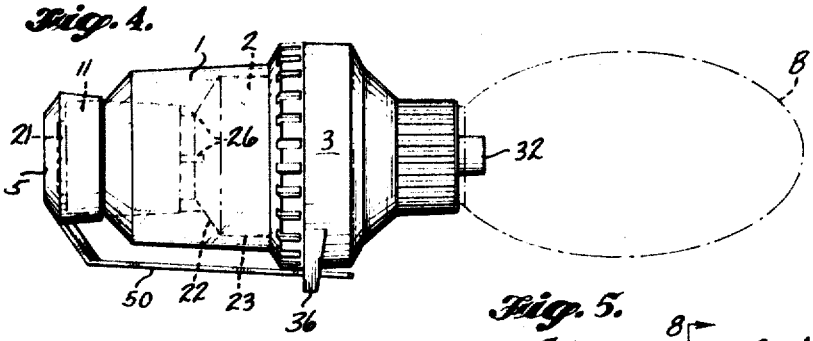
FIGURE 4 is a side elevational view of the assembled nebulizer, with its closure cap in place, ready for transporting, prepared for use.
Figure 9:
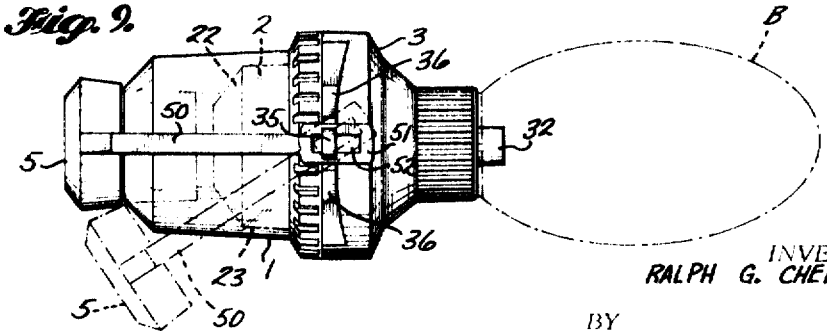

FIGURE 9 is a side elevational view, from a viewpoint 90° removed from that of FIGURE 4.

Figure 10:
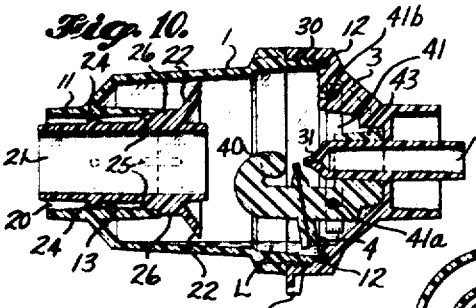

FIGURE 10 is an axial sectional view, similar to FIGURE 5, of a slightly modified form of the nebulizer.

The nebulizer, as stated above, can be readily molded of plastic material, and will be described as of such material, which has some inherent flexibility and resilience. It comprises an outer shell 1, of generally tubular shape, of transparent plastic. At one end it is formed with a sleeve 11, which projects within its interior, and which will normally project exteriorly of the shell 1. At its opposite end the shell 1 is formed for securement to and ready separation from a base 3; for example, these may be complementally threaded, at 10 and at 30. A sealing ring 12 received within a groove in the base that is aligned with the end of the shell 1 is compressed by screwing home the shell upon the base, which prevents leakage at this point. An inner nozzle 31 upstanding centrally of the base directs primary air from an external source, such as the hand bulb B secured to the exterior end 32 of nozzle 31, with entrained medicament, through the sleeve 11, as will appear more fully hereinafter.

The reference herein to primary air, delivered at the inner nozzle 31, is to the usual gas employed here, but the term "air" is to be understood as including any suitable gas, such as oxygen, oxygen-enriched air, oxygen and helium mixed, Freon, or other gas, supplied under some pressure.

A third principal part is the inner shell 2, which is normally of transparent plastic. This inner shell is formed with an integral tube 21 of a size to fit within the sleeve 11, spaced from the sleeve's interior wall, thereby to define an annular secondary air inlet passage 20. The tube 21 constitutes an outer nozzle, and preferably terminates somewhat beyond the outer end of sleeve 11; this spacing between the inlet for secondary air, at the outer end of sleeve 11, and the outlet for air and droplets at the outer end of tube 21, avoids conflict between the oppositely moving inlet and outlet airflows.

Liquid stored within the shell 1 will have access. while the nebulizer is being carried, to the air inlet passage 20. That passage is sufficiently small that it would be difficult to clean it thoroughly unless the tube 21 and sleeve 11 can be wholly separated, yet accuracy in their assembled relationship is necesary to proper functioning. In order to serve these several needs the shell 1 and its sleeve 11, and the shell 2 and its tube 21, are interengaged by relative axial movement, and by means that will insure their interengagement in correct operative relationship. The exterior of the tube, at widely spaced angular intervals, has axially separated spaced lugs 24 and 25 which engage the interior wall of sleeve 11 to center the tube within the sleeve. They obstruct the secondary air passage 20 negligibly. Shoulders 26 on the tube are located to engage the sleeve's inner end, thereby to govern the relative axial position of the two. The interior wall of the sleeve is slightly constricted at 13, and when the tube 21 is pushed to its operative position relative to the sleeve 11, the lugs 24 are so located that they snap past the constriction at 13. This holds the tube and sleeve, and the integral inner and outer shells, respectively, in correct operative relationship, against accidental displacement.

The primary function of the inner shell 2 is to distribute the inflowing secondary air rather uniformly outwardly so that it will not obstruct outflow of primary air through the outer nozzle 21, until it can be drawn uniformly inwardly towards the inner nozzle by the discharge from the inner nozzle, and will join with that discharge flow. While it has been found to function thus if it is merely flared, as at 22, within the interior end of sleeve 11, so as to direct the secondary air towards the interior walls of shell 1, it is preferred that it also include a skirt 23 that terminates in the vicinity of the discharge end of the inner nozzle 31. So arranged, the secondary air will mingle with the primary air only as the secondary air is drawn in the same direction as the primary air, and no counterflow or eddy currents can occur.

The inner nozzle 31, projecting from the base 3 towards the interior of the shell 1, and aligned with the outer nozzle 21, is arranged exteriorly of the base for connection to a source of primary air, as that term is defined above, under some pressure. As has already been explained, its externally projecting end 32 is shown as fitted with a hand bulb B, constituting such a source. Any other suitable source may be employed.

The space within the shell 1, closed by the base 3, receives a small amount of liquid. This is illustrated in FIGURES 5 and 10 at L. The liquid can be introduced through the outer nozzle 21. Within this liquid space is accurately located a separate body or assembly that consists of an eduction passage such as a capillary tube 4, a baffle such as the ball 40, and supporting structure including a locating ring 43 of a size and shape to fit closely the inwardly projecting discharge end of the inner nozzle 31. Located thus, the discharge from the nozzle 31 passes the discharge end of capillary tube 4. The pick-up end of that tube is in the same way located below the surface of liquid L, and discharge from nozzle 31 educts liquid from capillary tube 4, directing it towards the outer nozzle 21. Immediately in its path is the baffle 40. The liquid, impinging upon the baffle 40, is nebulized, or broken into tiny droplets constituting a fog or mist, and the primary air, and secondary air that mingles therewith, serves as a vehicle to convey such particles out at the discharge end of the outer nozzle.

The eduction passage will ordinarily take the form of what, in this art, is usually termed a capillary tube. It can take other forms, and any narrow passageway, within which liquid is caused to rise to the exit of nozzle 31 by the eduction effect of primary air moving past such exit, is to be understood as included within the terms "capillary tube" or "eduction passage," as such terms are used herein.

The separate body just described is small, and if it were capable of being wholly separated from the base when parts must be cleaned it might easily be lost or damaged. To avoid this the separate body is connected to the base in a manner that permits its removal for cleaning, but precludes usual or accidental complete separation. To this end a ribbon 41 of somewhat flexible plastic material is secured—for instance pivotally—at 41a to the separate body, and is similarly secured at 41b to the base 3. The latter connection, or at least one of the two connections, can be disengaged by forcing the resiliently deformable plastic, but will not disengage accidentally. The ribbon 41 is sufficiently stiff, and so curved, as to fit within the curve of the base. The separate body 4, 40, 43 can be lifted from the inner nozzle 31, yet the ribbon 41 retains it against complete separation from the base.

The outer end of outer nozzle 21, and of its surrounding sleeve 11, have a closure cap 5 fitted to them, by means of which spilling of liquid is avoided while the nebulizer is being carried in a handbag or a pocket. This is a part that could easily be lost, so it is secured to the nebulizer in a manner similar to the securement of the body 4, 40, 43. A somewhat flexible ribbon 50 of flexible plastic material is fixed to the cap 5, and at its opposite end it is anchored to the shell. A T-shaped stud 35 stands out from the periphery of the base 3, between spaced abutments 36. A head 51 on the end of the ribbon 50 is slotted, at 52, to fit the T-head of stud 35 when turned laterally, but the abutments preclude such turning unless intentional. The slot 52 permits the ribbon to move in the axial direction sufficiently to lift the cap 5 off the outer nozzle, or to reseat it thereon, and the rotatable mounting of the ribbon about its stud 35, even though limited, enables the cap to be pushed aside when the liquid is to be discharged. The limited flexibility of the ribbon will prevent its getting in the way.

In order to locate the separate body 4, 40, 43 correctly rotationally about the inner nozzle 31, a rim 33 surrounding the nozzle 31 is interrupted at 34, to receive a heel 44 of the separate body when the ring 43 is pressed home upon nozzle 31. The closure cap 5 should be beneath the outer nozzle 21 during usage of the nebulizer, and the heel 44 in its notch 34 assures that the pick-up end of capillary tube 4 will be lowermost, within the liquid L, when the nebulizer is held with the cap 5 below the nozzle 21.

I claim as my invention:

1. A nebulizer comprising an outer shell formed with an inwardly directed sleeve at one end, an inner shell formed with a tube fitting within and spaced from the inner end of said sleeve to define a secondary air inlet, and constituting an outer nozzle, said inner shell flaring at the inner end of its tube to direct the inflowing secondary air along the interior wall of the outer shell, a base removably secured to the outer shell, at its end opposite the sleeve, to define within that shell a liquid space, an inner nozzle carried by said base in alignment with and directed through said tube, said inner nozzle being arranged, exteriorly of the base, for connection to a source of primary air, and means, including an eduction passage communicating at one end with the liquid space, located intermediate the inner and outer nozzles, for discharging a mist of such liquid, with a vehicle of primary and secondary air, through the outer nozzle.

2. A nebulizer as in claim 1, the inner shell including a skirt projecting towards the base from its flared periphery, to the vicinity of the eduction passage, but spaced from the interior wall of the outer shell.

3. A nebulizer comprising an outer shell closed to define a liquid space, and formed with a sleeve, an inner shell within said outer shell and formed with a tube fitting within said sleeve and constituting an outer nozzle, means within the outer shell to pick up and discharge a liquid mist through said outer nozzle from the liquid space, said sleeve and tube including means complementally engageable by their relative axial movement to retain the tube and the inner shell of which it is a part interengaged and correctly positioned relative to said pick-up and discharge means, but spaced apart throughout substantially their entire peripheral surfaces.

4. A nebulizer as in claim 3, wherein the inner wall of the sleeve is constricted between its ends, the outer wall of the tube having a series of radial spacers angularly spaced about it, axial stop means interengageable between the tube and the sleeve to limit their relative axial movement, and the radial spacers being located axially relative to said axial stop means to move past the sleeve's constriction just prior to interengagement of the axial stop means.

5. A nebulizer as in claim 3, wherein the tube projects farther outwardly than the surrounding sleeve, at their outer ends, the liquid pick-up and discharge means for the mist being directed outwardly axially of the tube.

6. A nebulizer comprising an outer shell and a removable base cooperating to define a liquid space, means opposite said base defining an outer nozzle for discharge of liquid from such space in the form of a mist, an inner nozzle projecting into the interior of said shell from the base, and towards said outer nozzle, said inner nozzle being arranged exteriorly of the base for connection to a source of primary air, a separate body disposed interiorly of the shell, said separate body comprising a capillary tube arranged at its pick-up end for communication with the liquid space and at its delivery end aligned with the discharge from said inner nozzle, a baffle disposed intermediate the delivery end of the capillary tube and said outer nozzle, a ring fitting about the inner nozzle to position said separate body correctly relative to the two nozzles and to the liquid space, and a flexible ribbon secured at one end to said separate body and anchored at its other end to said base, whereby the ring of the separate body is removable from the inner nozzle, but the separate body remains tied to the base.

7. A nebulizer comprising an outer shell formed with a sleeve, but otherwise closed to define a liquid space, an inner shell within said outer shell and formed with a tube fitting within and spaced from said sleeve, constituting an outer nozzle, means within the outer shell to pick up liquid from the liquid space and to discharge it as a mist through said outer nozzle, a removable closure cap arranged to fit and close the outer end of the sleeve and tube, a flexible ribbon interconnecting said closure cap and the outer shell, said ribbon being slotted lengthwise at one end, and a stud at this end projecting from the member to which it connects, through said slot, to enable movement of the cap lengthwise of the sleeve and tube, for engagement therewith or disengagement therefrom.

8. A neubilizer as in claim 7, wherein the stud is T-headed, the T-head being disposed transversely of the ribbon's slot, and abutments upon the member to which the ribbon connects, limiting rotation of the ribbon about the stud, thereby preventing accidental disengagement of the ribbon from the stud.

9. A nebulizer as in claim 8, wherein the ribbon is slotted at its end distant from the closure cap, and wherein the T-shaped stud is outsanding from the shell, in position to be engaged with one end of the slot when the cap is fitted upon the outer nozzle, and with the other end thereof when the cap is removed, the T-head of said stud being disposed in relation to the abutments to retain the ribbon unless the same is rotated angularly about the stud from its fitted-on position, beyond the amount of rotation permitted by the abutments.

10. A nebulizer comprising an outer shell formed with a sleeve at one end projecting both inwardly and outwardly of the shell, an inner shell formed with a tube spaced from but fitting within said sleeve by their relative axial movement, to define between them a secondary air inlet, said inner shell flaring within the outer shell to direct inflowing secondary air along the interior wall of the outer shell, a base removably secured to and closing the outer shell, opposite its sleeve, and cooperating with the outer shell to define an interior liquid space, an inner nozzle projecting inwardly from the base towards the outer nozzle, and arranged exteriorly of the base for connection to a source of primary air, a separate body within the outer shell, said separate body comprising a locating ring surrounding the inner nozzle, a capillary tube opening at its pick-up end to the liquid space, and at its discharge end registering with the discharge from the inner nozzle, and a baffle supported intermediate the discharge end of the capillary tube and the outer nozzle, a flexible ribbon anchored at one end to the separate body and at its other end to the base, a closure cap fitting upon the outer end of the outer nozzle, and a second flexible ribbon anchored at one end to said cap and at its other end to the base, and arranged to permit axial removal and replacement of said closure cap, and its movement aside for use.

*11. A nebulizer comprising an outer shell of generally tubular form, a transverse base closing one end of the outer shell, an inner shell of generally tubular form mounted within said outer shell substantially on a common longitudinal axis therewith, said inner shell having a longitudinally extending tubular portion the interior of which opens toward the base and which tubular portion terminates short of contact with said base so as to form a substantially annular gap therebetween, said portion being spaced transversely inward from the outer shell along the longitudinal extent of said portion so as to form a longitudinal flow space of substantially annular form between the shells communicating with the interior of said portion through said gap, said inner shell further comprising a tubular outer nozzle directed away from said base and communicating with the interior of said portion, means providing an entrance opening through said outer shell at a location spaced longitudinally from said base so as to lead secondary air into said flow space, and medicant liquid spray-producing means operably positioned adjacent the base and having elements cooperable to form a spray of finely divided liquid particles and primary air directed substantially axially away from said base into the interior of said inner shell tubular portion for admixture thereof in coaxial confluence with secondary air flowing radially inwardly through said gap after traversing said flow space from said opening.*

*12. The nebulizer defined in claim 11, wherein the inner shell tubular portion flares interiorly and exteriorly toward the base along at least part of its longitudinal extent.*

References Cited

The following references, cited by the Examiner, are of record in the patented file of this patent or the original patent.

UNITED STATES PATENTS

| | | | |
|---|---|---|---|
| 2,139,289 | 12/1938 | Skoda | 222—522 |
| 2,192,020 | 2/1940 | Stubler | 222—522 |
| 2,726,896 | 12/1955 | McKinnon | 239—338 |
| 2,951,644 | 9/1960 | Mahon et al. | 239—338 |
| 3,018,971 | 1/1962 | Cheney | 239—338 |
| 3,172,406 | 3/1965 | Bird et al. | 128—173 |

M. HENSON WOOD, JR., Primary Examiner

B. BELKIN, Assistant Examiner

U.S. Cl. X.R.

222—523; 239—370, 505, 514